US007940175B2

(12) United States Patent
Peter et al.

(10) Patent No.: US 7,940,175 B2
(45) Date of Patent: May 10, 2011

(54) DEVICE WITH A DETECTABLY DESIGNED WATER TRAP AND PROCESS FOR DETECTING A WATER TRAP

(75) Inventors: Gerd Peter, Lübeck (DE); Thomas Maxeiner, Lübeck (DE)

(73) Assignee: Dräger Medical GmbH, Lübeck (DE)

( * ) Notice: Subject to any disclaimer, the term of this patent is extended or adjusted under 35 U.S.C. 154(b) by 673 days.

(21) Appl. No.: 11/877,799

(22) Filed: Oct. 24, 2007

(65) Prior Publication Data

US 2008/0173306 A1     Jul. 24, 2008

(30) Foreign Application Priority Data

Dec. 9, 2006    (DE) ......................... 10 2006 058 164

(51) Int. Cl.
     *G08B 21/00*      (2006.01)
(52) U.S. Cl. ....................................... 340/540
(58) Field of Classification Search .................... 340/540
See application file for complete search history.

(56) References Cited

U.S. PATENT DOCUMENTS

| 4,440,162 | A | * | 4/1984 | Sewell et al. ............. 128/202.22 |
| 5,097,416 | A | * | 3/1992 | Matthews ....................... 700/91 |
| 5,898,375 | A | * | 4/1999 | Patterson ...................... 340/612 |
| 6,117,214 | A | * | 9/2000 | Peter et al. ........................ 96/6 |
| 6,250,132 | B1 | * | 6/2001 | Drzewiecki .................... 73/23.2 |
| 6,483,434 | B1 | * | 11/2002 | UmiKer ..................... 340/572.1 |
| 7,661,582 | B2 | * | 2/2010 | Mollstam ..................... 235/375 |
| 2003/0023182 | A1 | * | 1/2003 | Mault et al. .................. 600/532 |
| 2003/0105407 | A1 | * | 6/2003 | Pearce et al. ................. 600/532 |
| 2004/0124988 | A1 | * | 7/2004 | Leonard et al. .............. 340/612 |
| 2005/0211761 | A1 | * | 9/2005 | Anttila et al. ................ 235/376 |
| 2006/0151624 | A1 | * | 7/2006 | Grundler et al. ............... 237/67 |
| 2007/0018833 | A1 | * | 1/2007 | Higashionji et al. ....... 340/572.7 |
| 2007/0175471 | A1 | * | 8/2007 | Schermeier et al. ..... 128/200.24 |

FOREIGN PATENT DOCUMENTS

| DE | 199 01 590 C1 | 7/2000 |
| EP | 1 579 884 A1 | 2/2005 |

* cited by examiner

*Primary Examiner* — George A Bugg
*Assistant Examiner* — Naomi Small
(74) *Attorney, Agent, or Firm* — McGlew and Tuttle, P.C.

(57) ABSTRACT

A device with a water trap. The device has a gas sensor and is designed to send a gas sample flow through the water trap (2) and to feed it to the gas sensor (3). The water trap (2) is designed to be separably connected to the device. The device has a mount for connection to the water trap. The water trap (2) has a radio frequency marking (5). The device has a radio frequency detection device (6) with a detection area (7) for the radio frequency marking, which is designed to detect the radio frequency marking in the detection area and to generate a marking signal, which represents marking information of the radio frequency marking. The device is designed to be controlled as a function of the marking signal.

19 Claims, 4 Drawing Sheets

DEVICE WITH A DETECTABLY DESIGNED WATER TRAP AND PROCESS FOR DETECTING A WATER TRAP

CROSS REFERENCE TO RELATED APPLICATIONS

This application claims the benefit of priority under 35 U.S.C. §119 of German Patent Application DE 10 2006 058 164.4 filed Dec. 9, 2006, the entire contents of which are incorporated herein by reference.

FIELD OF THE INVENTION

The present invention relates to a device with a water trap. The device has a gas sensor and is designed to send a sample gas flow through the water trap and to feed it to the gas sensor. The water trap is designed to be separably connected to the device. The device has a mount for connection to the water trap. The device is, for example, a monitor device or a respiration device.

BACKGROUND OF THE INVENTION

A water trap for a sample gas flow is known from DE 199 015 90 C1. The water trap has a housing, which can be separably connected to a holder. The housing has a tank for receiving liquid.

An arrangement in connection with a patient circuit and absorber means is known from EP 1 579 884 A1. The arrangement has information transfer means and electronic means and an electronically programmed transponder with information. The transponder is connected to the absorber means. The information transfer means are designed to communicate with the transponder, and the electronic means are designed to read procedures from a database, obtained from an anesthesia/ventilation system and via the information transfer means from the transponder, which is connected to the absorber means.

The problem of water traps known from the state of the art, for example, also of the water trap known from DE 199 015 90 C1, is that microorganisms may accumulate in the water trap, especially in a container of the water trap. The use time of the water trap is therefore limited, and use of the water trap over a limited time period is recommended. In practice, the operating staff notes a date at which a new water trap is connected to the respiration device. After the end of a predetermined time period, which is preset, for example, by the manufacturer of the water trap, the water trap shall be changed by the operating staff and replaced with a new water trap.

SUMMARY OF THE INVENTION

The basic object of the present invention is to improve a device in terms of the handling of a water trap.

According to the invention a device is provided, in which the water trap has a radio frequency marking. The device has a radio frequency detection device with a detection area for the radio frequency marking, which is designed to detect the radio frequency marking in the detection area and to generate a marking signal, which represents marking information of the radio frequency marking. The device is designed to be controlled as a function of the marking signal. As a result, the connected state of the water trap to the device can be advantageously detected by the device. For example, the device may be advantageously designed to detect the duration of the connected state of the water trap.

In a preferred embodiment, the device has a time counter, which is connected at least indirectly to the radio frequency detection device and is designed to generate, as a function of the marking signal, especially of at least the presence of the marking signal, a time period, which represents a duration during which the water trap is connected to the device, to compare the time period with a predetermined run time period and to generate a comparison result. The device is designed, furthermore, to generate, as a function of the comparison result, a run signal, which represents a time course of the predetermined run time period. The device is designed to be controlled as a function of the run signal. It can be advantageously ensured as a result that the water trap is not connected to the device for a duration longer than the duration corresponding to the run time period.

For example, the device can be controlled as a function of the run signal such as to generate an audio or visual warning signal as a function of the run signal and to represent this. The device may have for this, for example, a display unit or a light signal transmitter, which are designed to generate the warning signal.

In an advantageous embodiment, the device is designed to be blocked or released at least partially as a function of the marking signal. The device is designed, likewise in a preferred manner, to be blocked or released at least partially as a function of the run signal. It can be advantageously ensured as a result that a water trap is not connected to the device for a duration longer than the duration of the run time period. For example, the device can be blocked or released at least partially such that predetermined control elements of the device are released or blocked. For example, the device may be designed to continue a measuring operation after partial blocking as a function of the marking or run signal in order to be restarted after stopping. In another embodiment, components of the device can be blocked or released. Components may be, for example, a control unit, control elements, a measured gas pump or a predetermined operating function.

The run time period is represented by the marking information in a preferred embodiment of the device. For example, a predetermined use time can be assigned to a certain water trap, which has a predetermined liquid volume.

In a preferred embodiment, the marking information represents a code, which is assigned to a certain water trap, especially a predetermined water trap. For example, the code may represent a date of manufacture, a serial number or a combination of these. It can thus be advantageously ensured that a water trap connected to the device after starting a time counter must be separated from the device and replaced with another water trap. The device may be advantageously designed for this to detect a code represented by the marking function and to store it in memory. Furthermore, the device may be designed to interrupt a counting by means of the time counter, especially the generation of the time period as a function of the marking signal and to continue the generation of the time period when the marking signal is again detected. The device can especially advantageously continue or restart the time counter as a function of the code represented by the marking information. For this, the device can compare the code detected in case of connection with the code already stored in the memory and restart or continue the generation of the time period by the counting device and as a function of a comparison result.

In a preferred embodiment, the water trap has a container for an especially hydrophilic liquid, and the radio frequency marking is arranged within the container and can be subject to buoyancy in the especially hydrophilic liquid. The radio frequency marking preferably has a color different from the liquid, especially body color, and the container is transparent to electromagnetic radiation in the visible range at least in one area of the container wall. The radio frequency marking may preferably be self-radiating and have for this, for example, a light, especially a luminescence diode, which radiates light through the container wall.

In a preferred embodiment, the radio frequency marking is designed to receive marking information and to store it again in a readable form. The radio frequency detection device is designed in this embodiment to send marking information to the radio frequency marking and store it there. A connection time of a certain water trap to the device can be advantageously detected as a result. The device may be designed for this, for example, to generate—before the water trap is separated from the device—marking information, for example, in the form of a marking data set, which represents the time period generated by the time counter, and to send this marking information or the marking data set by means of the radio frequency detection device, especially a read-write radio frequency detection device, to the radio frequency marking and to store it there. When the previously separated water trap is reconnected to the device, the device can detect the marking information, especially the connection time represented by the time period, for example, by means of the radio frequency detection device, and to store it in memory.

The time counter may also be designed, in a likewise preferred manner, to continue counting as a function of the stored time period. A connection time of a predetermined water trap can be advantageously detected in this manner regardless of how often the predetermined water trap is separated from the device and operated further with the same device or with another device.

Preferred embodiments of a radio frequency detection device are designed to operate in a frequency range of 30 kHz to 500 kHz, in a frequency range of 800 MHZ to 950 MHZ or in a frequency range of 1 GHz to 3 GHz. The radio frequency detection device is preferably designed to operate at a frequency of 125 kHz or at a frequency of 13.56 MHZ. The radio frequency detection device and the radio frequency marking may operate with one of the following modulation methods or a combination of the following modulation methods, for example, when sending a marking signal representing the radio frequency marking:
  FM (FM=frequency modulation);
  AM (AM=amplitude modulation);
  FSK (FSK=frequency shift keying);
  ASK (ASK=amplitude shift keying);
  PSK (PSK=phase shift keying).

The radio frequency detection device can preferably detect the radio frequency marking by means of load modulation. The radio frequency detection device can provide the radio frequency marking with sending energy. For example, the radio frequency marking may have for this an energy storage unit and store the received sending energy and use it to send back a response sending signal representing the marking information. Active radio frequency marking, which has an energy source for sending the marking information, is also conceivable.

A water trap for a respiration device may advantageously have a radio frequency marking. The radio frequency marking is preferably arranged in the area of the water trap. The radio frequency marking is preferably also coupled with or connected to the water trap. The radio frequency marking may be enclosed for this, for example, in a container of the water trap, bonded to same or welded on a housing or a part of the water trap. The radio frequency marking may advantageously be subject to buoyancy in a liquid being stored in a container of the water trap.

The present invention also pertains to a process for detecting a water trap with a radio frequency marking, which the water trap is separably connected to a device, comprising the steps:
  Detection of the radio frequency marking of the water trap and of a marking information represented by the radio frequency marking, and generation of a marking signal representing the marking information;
  Starting of a time counter for incrementing a time value as a function of the marking signal; and
  Generation of a run signal as a function of the reaching of a predetermined time value and controlling the device as a function of the run signal.

In an advantageous embodiment, the process includes the step:
  Blocking or releasing of components of the device as a function of the run signal.

In an advantageous embodiment, the process includes the step:
  Stopping or restarting or continuing a counting by the time counter as a function of the marking signal.

The process preferably also includes the step:
  Sending of the time value to the radio frequency marking and storing of the time value in the radio frequency marking after stopping the time counter.

The present invention will be explained below on the basis of figures and other exemplary embodiments. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which the preferred embodiment of the invention is illustrated.

DESCRIPTION OF THE PREFERRED EMBODIMENT

Figure 1:
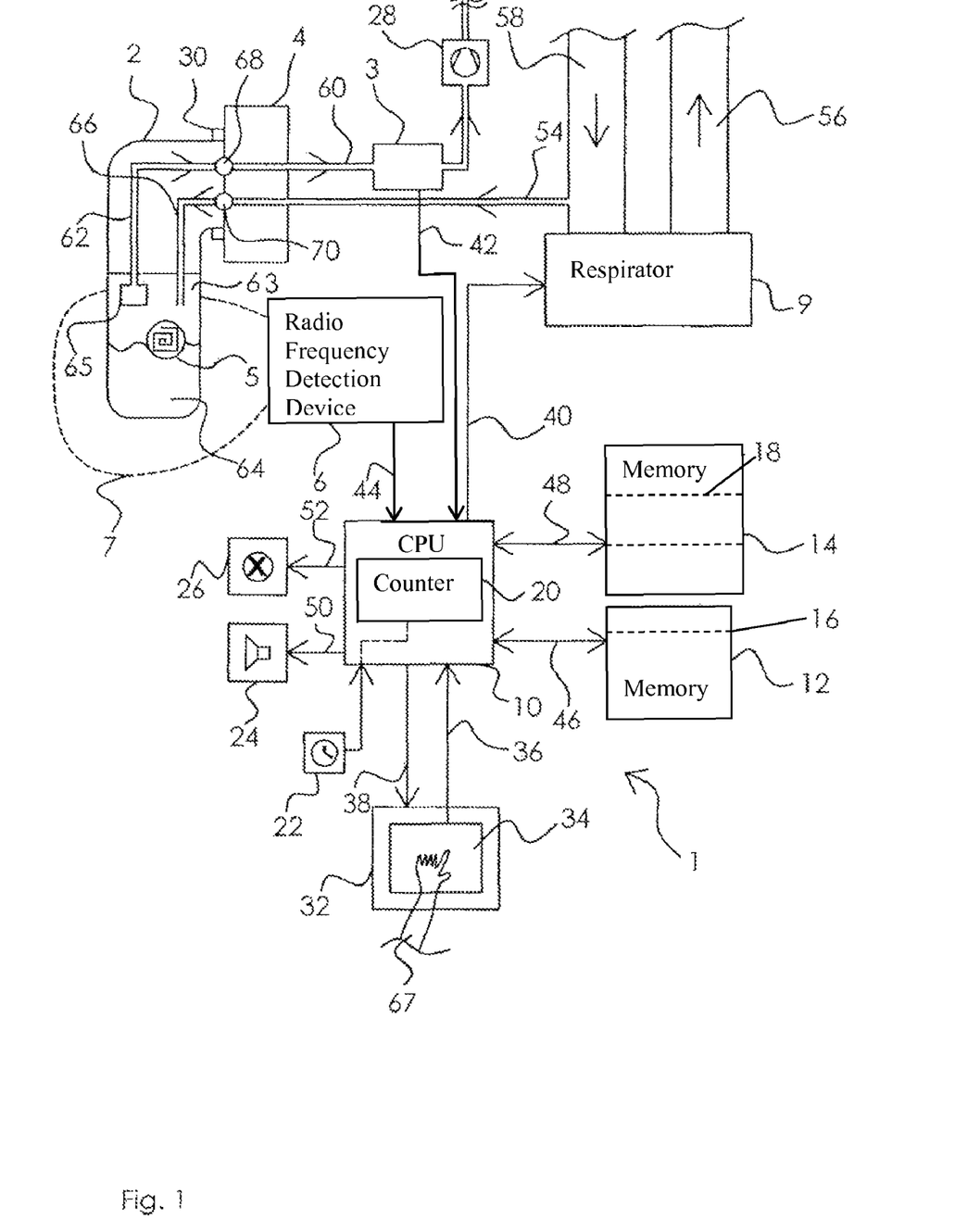
FIG. 1 is a schematic view showing an exemplary embodiment for a respiration device.

Referring to the drawings in particular, FIG. 1 schematically shows an exemplary embodiment for a respiration device 1. The respiration device 1 has a water trap 2, which is designed for separable connection to the respiration device. The respiration device 1 has for this a mount 4 for connection to the water trap 2. The respiration device 1 also has a gas sensor 3. The water trap 2 has a radio frequency marking 5, which is enclosed in a container of the water trap 2. The radio frequency marking 5 is designed to be subject to buoyancy in a liquid, especially in a hydrophilic liquid, for example, one containing water. The respiration device 1 also has a radio frequency detection device 6, which is designed to detect the radio frequency marking 5 by means of load modulation and to generate a marking signal, which corresponds to marking information being stored in the radio frequency marking 5. The respiration device 1 also has a respirator 9, which may be designed as a breathing apparatus or as an anesthesia apparatus. The respiration device 1 also has a control unit comprising a central processing unit 10, a memory 12 and a memory 14. The memory 12 is designed as a buffer memory and is designed to store data sets, of which the data set 16 is mentioned as an example. The memory 14 is designed to store data sets, of which the data set 18 is mentioned as an example. The respiration device 1 also has a time counter 20, which is part of the central processing unit 10 in this exemplary embodiment. The time counter 20 is connected to a timer 22, which is designed to generate a time signal forming a time basis. The timer 22 may have, for example, a quartz resonator for generating the time signal. The respiration device 1 also has a sound generator 24 for generating an audio warning signal. The respiration device 1 also has a signal light 26, which is designed to send especially a light warning signal, especially one visible from a great distance, in the form of visible electromagnetic radiation. The respiration device 1 also has a pump 28, which is connected to the gas sensor 3 on the inlet side and, for example, to the air surrounding the respiration device 1 on the outlet side. The water trap 2 is separably connected to the mount 4 by means of a plug-type connection 30. The water trap 2 may have cam or projection areas for this, which can be introduced each into corresponding recesses of the mount 4, which are designed to extend behind the cam or projection areas of the water trap 2 in a positive-locking manner such that the water trap 2 is detachably connected to the mount 4. The cam or projection areas of the water trap 2 and the recesses and projections of the mount 4 may be designed and arranged in relation to one another for this, for example, such that the water trap 2 can be introduced into the recesses of the mount 4, for example, by a translatory motion along a connection axis and secured against separation along the connection axis by a subsequent rotary motion about the connection axis in a positive-locking manner.

The respiration device 1 also has an input unit 32 designed as a display or image display unit with a touch-sensitive surface 34. The touch-sensitive surface 34 is designed to generate, as a function of being touched, for example, by a user's hand 67, a user interaction signal, which represents the site at which the touch-sensitive surface 34 is touched. The touch-sensitive surface is connected to the central processing unit 10 via a connection line 36. The central processing unit 10 is connected on the output side to the image reproduction unit of the input unit 32 via a connection line 38. The central processing unit 10 is connected on the output side to the respirator 9 via a connection line 40 and is designed to generate a control signal for controlling the respirator and to send this signal to the respirator 9 via the connection line 40.

The gas sensor 3 is connected on the output side to the central processing unit 10 via a connection line 42 and is designed to detect a gas component in a sample gas flow, especially photo-optically, for example, infrared optically and/or electrochemically, and to generate a sensor signal, which represents the gas component. The gas component may be, for example, oxygen, carbon dioxide, laughing gas or anesthetic. The central processing unit 10 is connected to the memory 12 via a connection line 46 and to the memory 14 via a connection line 48. The connection lines 46 and 48 are each of bidirectional design and may be formed, for example, by a bidirectional data bus each.

The central processing unit 10 is connected on the output side to the sound generator 24 via a connection line 50 and to the signal light 26 via a connection line 52. The respirator 9 is connected on the gas flow outlet side to a respiration line 56, which encloses a lumen for guiding a gas. The respirator 9 is connected to a respiration line 58 on the gas flow inlet side. The respiration line 58 encloses a lumen for guiding a gas. The respiration line 58 is connected to a sample gas line 54, which encloses a lumen for guiding the sample gas flow. The lumen of the sample gas line 54 is connected to the lumen of the respiration line 58. The sample gas line 54 connects the respiration line 58 to a lumen of the mount 4. The lumen of the mount 4, which lumen is connected to the sample gas line 54, has an opening 70 at the connection of the water trap 2 for connection to the water trap 2. The water trap 2 has a connection line 66, which encloses a lumen for guiding the sample gas. The sample gas line 66 of the water trap 2 leads into a cavity 63 of the water trap 2, which cavity is enclosed by a container wall of the water trap 2. A sample gas line 62 of the water trap 2 connects the cavity 63—in the connected state of the water trap 2 to the mount 4—via an opening 68 of the mount 4, via a lumen connected to the opening 68 and via a sample gas line 60, which encloses a lumen for guiding the sample gas, to the gas sensor 3, which is connected to the sample gas line 60 on the inlet side. In the area of an end opening into the cavity 63, the sample gas line 62 of the water trap 2 has a filter membrane 65, which is arranged between the lumen enclosed by the sample gas line 62 and the cavity 63. The filter membrane 65 is permeable to gases and water-repellent. The filter membrane may have for this, for example, polytetrafluoroethylene. Exemplary embodiments of such a filter membrane are a Goretex® membrane or a Durapel® membrane. The radio frequency detection device 6 is connected to the central processing unit 10 via a connection line 44. The connection line 44 is of a bidirectional design.

The mode of action and the cooperation of the components of the respiration device 1 will be explained below:

The radio frequency detection device 6 can detect the radio frequency marking of the water trap 2 arranged in the detection area 7. This means that the water trap 2 is connected to the mount 4. The radio frequency marking 6 can read the radio frequency marking 5—for example, by means of load modulation—and generate a marking signal, which represents marking information of the radio frequency marking 5. The marking information may be a date of manufacture or a serial number or a combination of these. The radio frequency detection device can send the marking signal to the central processing unit 10 via the connection line 44.

By means of the time signal generated by the timer 22 and of the marking signal, the central processing unit 10 can generate a data set, which represents the marking information, especially the serial number of the water trap 2 and a current date, namely, the date of putting the water trap 2 into operation. The central processing unit 10 can start the time counter 20, which can generate a time data set representing a time period, as a function of the marking signal received via the connection line 44.

The time counter 20 can increment the time data set as a function of the time signal generated by the timer 22 in a time-dependent manner. The time data set thus represents a time period that represents a duration during which the water trap 2 is put into operation. The central processing unit 10 can store the marking data set in the memory 14 via the connection line 48. The data set 18 may form, for example, a marking data set. In case of removal of the water trap 2 from the mount 4, and also of removal of the radio frequency marking 5 from the detection area 7 of the radio frequency detection device 6, the radio frequency detection device 6 can generate a stop signal and send this via the connection line 44 to the central processing unit—or the central processing unit 10 can detect the absence of a marking signal generated continuously in time, for example, at predetermined time periods by the radio frequency detection device 6 and stop the time counter 20 as a function of the stop signal or as a function of the absence of the marking signal. The central processing unit 10 can then generate a time data set, which is assigned to the marking data set of the water trap 2, or a data set that represents the duration of the time during which the water trap is connected to the mount 4, which time is detected by the time counter 20, and the serial number of the water trap 2, and store this data set in the memory 12 via the connection line 46. The data set 16 is mentioned as an example and may be a data set representing a serial number and a connection time.

The memory 12 and the memory 14 may form together, for example, a common memory or form together a look-up memory. A marking data set, which represents a serial number of a water trap, can be assigned in a look-up memory to a time data set, which represents a connection time.

In case of reconnection of the water trap 2 to the mount 4, the radio frequency detection device 6 can detect the radio frequency marking 5 of the water trap 2 and generate a corresponding marking signal and send same via the connection line 44 to the central processing unit 10. The central processing unit 10 can then read the data set 16 via the connection line 46 from the memory 12 and further increment the time period represented by the data set 16 by means of the time counter 20 and generate a time data set, which represents the incremented time period, for example, for each incrementation step. The incremented time data set can be stored in the memory 12, for example, via the connection line 46 and stored there. At the time of a new incrementation operation by the time counter 20, the time data set can be read from the memory 12 via the connection line 46, and an incremented data set, which represents a longer connection time, can be stored again in the memory 12.

Before the respiration device 1 is started, it is possible to preset, for example, a maximum connection time of the water trap 2 to the mount 4. The central processing unit 10 can generate for this a corresponding data set, which represents a maximum connection time, as a function of a user interaction signal received via the connection line 36, and to store this data set in the memory 12. In another embodiment, the maximum connection time may be comprised, for example, by the marking information of the radio frequency marking 5. The marking signal can represent the maximum connection time of the water trap 2 in this exemplary embodiment. The maximum connection time may be represented, for example, by the marking data set, for example, the data set 18. The central processing unit 10 compares the time data set generated by the time counter 20, for example, at predetermined time periods, with the marking data set representing the maximum connection time and thus detect that the maximum connection time of the water trap 2 to the mount 4 and thus to the respiration device 1 has been exceeded.

In case the maximum connection time is exceeded, the central processing unit 10 can generate a warning signal and send this to the sound generator 24 or to the signal light 26, for example, via the connection line 50 and/or via the connection line 52.

As an alternative or in addition, it is possible to display the exceeding of the maximum connection time in the input unit 32.

In another embodiment, the central processing unit 10 may be designed to stop the operation of the pump 28 depending on whether the maximum time during which the water trap 2 is connected to the mount 4 is exceeded.

In another advantageous embodiment of the respirator 1, separation of the water trap 2 from the mount 4 can be initiated by a user interaction signal sent via the connection line 36. As a function of such a user interaction signal, the central processing unit 10 can generate a marking data set, which represents the connection time generated by the time counter 20 and send this data set to the radio frequency detection device 6 via the connection line 44. The radio frequency detection device 6 can send the marking data set to the radio frequency marking 5 and store it there. The radio frequency detection device is designed in this embodiment for writing and reading a radio frequency marking. The radio frequency marking 5 is designed in this embodiment for being written and being read. The radio frequency marking 5 may be an active or passive radio frequency marking. The radio frequency marking 5 may be advantageously subject to buoyancy in a liquid, especially in water or in a hydrophilic liquid 64. In case of a transparent container wall of the water trap 2, a liquid level of the liquid 64 can be visibly perceived from the outside from the local position of the radio frequency marking 5 within the cavity 63 of the water trap 2. The radio frequency marking 5 can assume two functions in this manner, namely, the display of the liquid level of the liquid 64, and the storing of marking information, which is provided for being read by the radio frequency detection device 6.

During the operation of the water trap 2, the pump 28 can generate a vacuum at the outlet of the gas sensor 3 and thus generate a sample gas flow beginning from the lumen 58 via the sample gas line 54, through the cavity 63 of the water trap 2, through the filter membrane 65 and via the sample gas line 62, the sample gas line 60 on the inlet side towards the gas sensor 3. The gas sensor 3 can generate a sensor signal as a function of the detected gas component of a gas to be detected and send this sensor signal to the central processing unit 10 via the connection line 42. The central processing unit 10 can generate a control signal for controlling the respirator 9 as a function of the sensor signal and send this control signal to the respirator 9 via the connection line 40.

A respiration arrangement may comprise the respiration device 1 without the water trap 2, and the water trap 2. A water trap 2 for the respiration arrangement may have a radio frequency marking.

Figure 2:
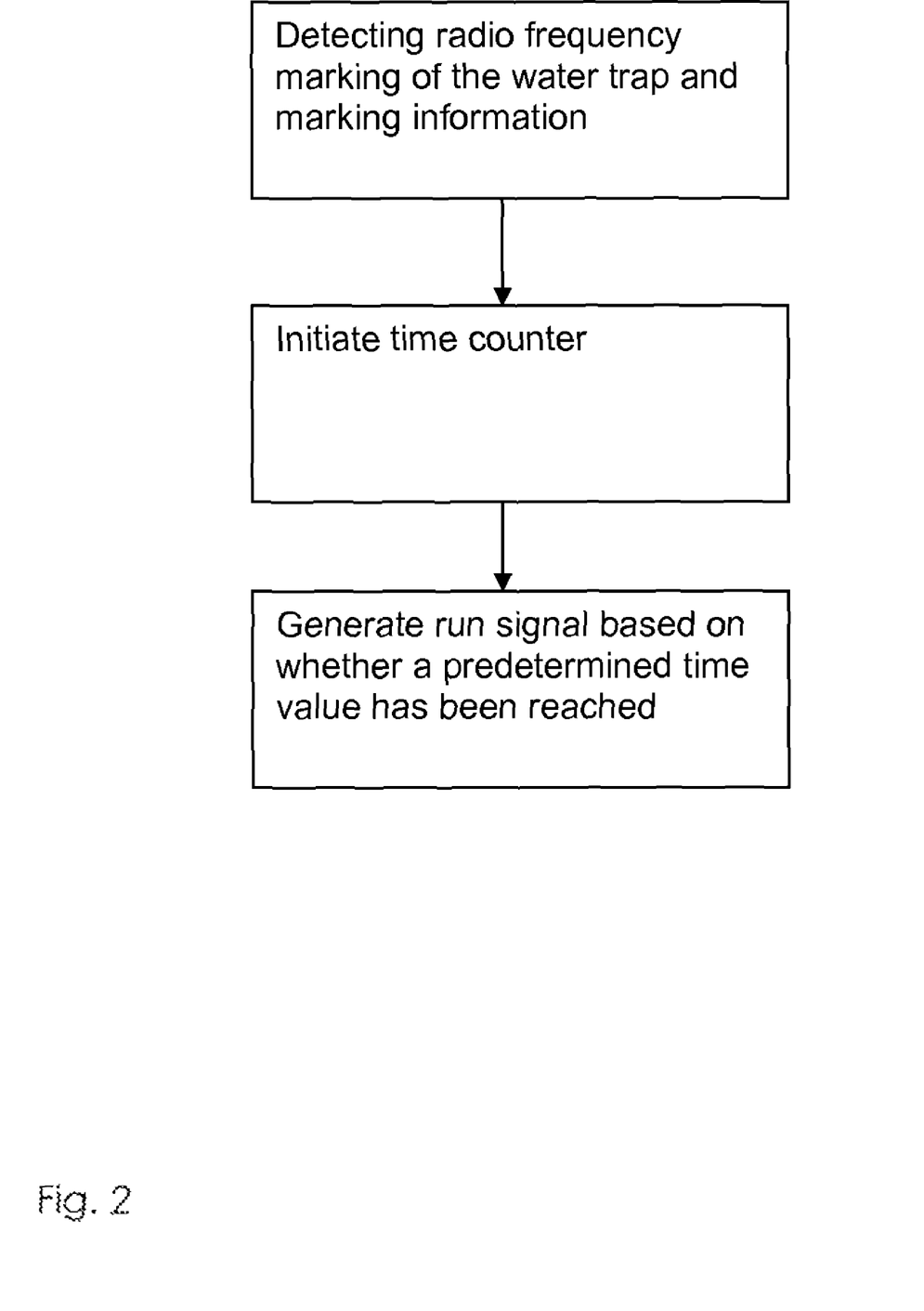
FIG. 2 is a schematic view showing an exemplary embodiment for a process for detecting a water trap with a radio frequency marking, which water trap is separably connected to a respiration device.

FIG. 2 schematically shows a process for detecting a water trap separably connected to a respiration device with a radio frequency marking. A radio frequency marking of the water trap and marking information represented by the radio frequency marking are detected in step 70 and a marking signal representing the marking information is generated. A time counter, which increments a time value, is started in step 72 as a function of the marking signal. A run signal is generated in step 74 depending on whether a predetermined time value has been reached and the respiration device is controlled as a function of the run signal.

Figure 3:
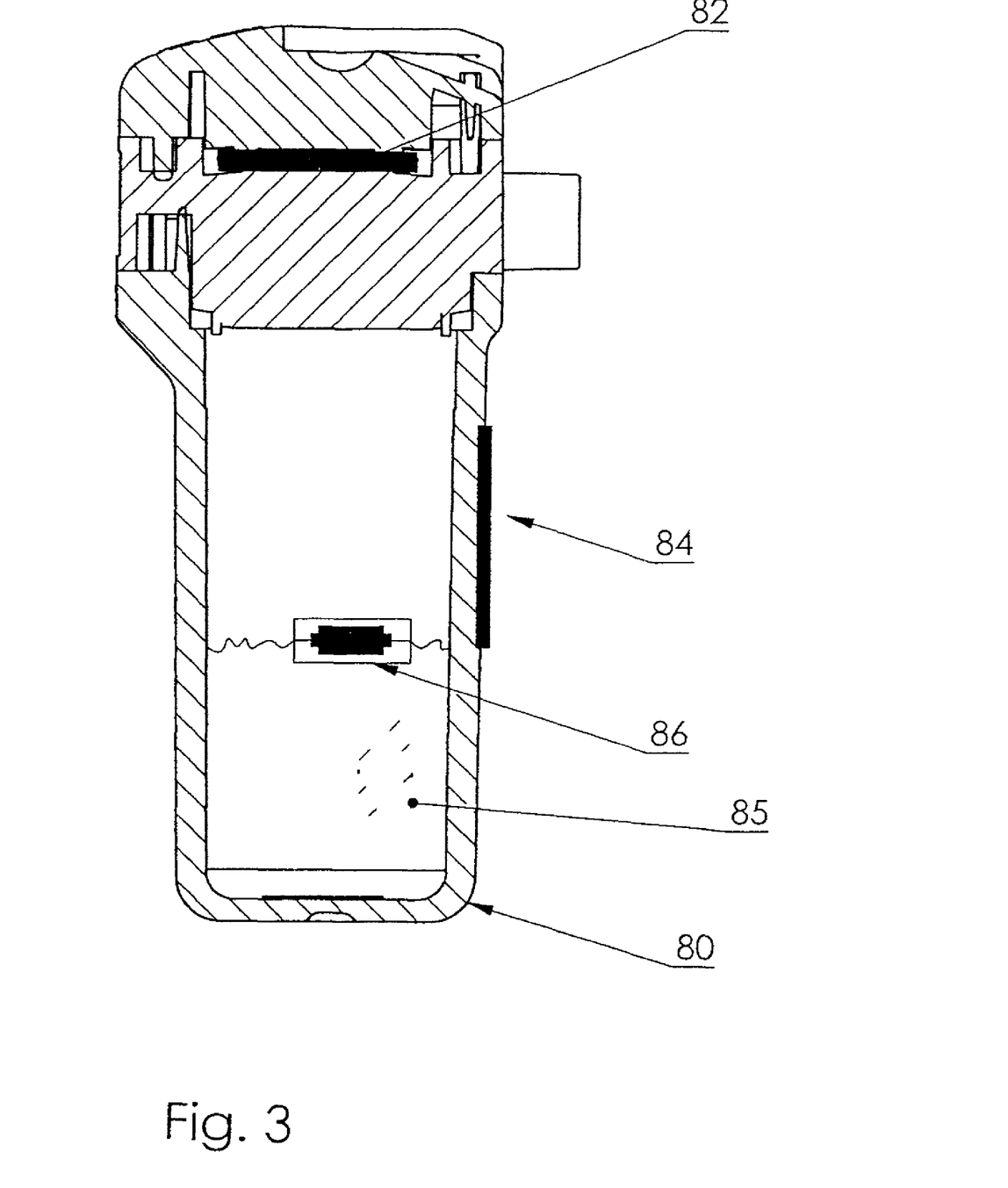
FIG. 3 is a schematic view showing an exemplary embodiment for a water trap.

FIG. 3 schematically shows an exemplary embodiment for a water trap 80. The water trap 80 has a radio frequency marking 82, which is arranged in the head of the water trap 80 invisibly from the outside. In another exemplary embodiment, a radio frequency marking is bonded to the water trap. FIG. 3 also shows a radio frequency marking 84, which is bonded to the water trap 80. In another embodiment, a radio frequency marking 86 is arranged in the water trap 80 and designed to be subject to buoyancy in a liquid 85.

The radio frequency markings 82, 84 and 86 may be embodied at a water trap independently from one another.

Figure 4:
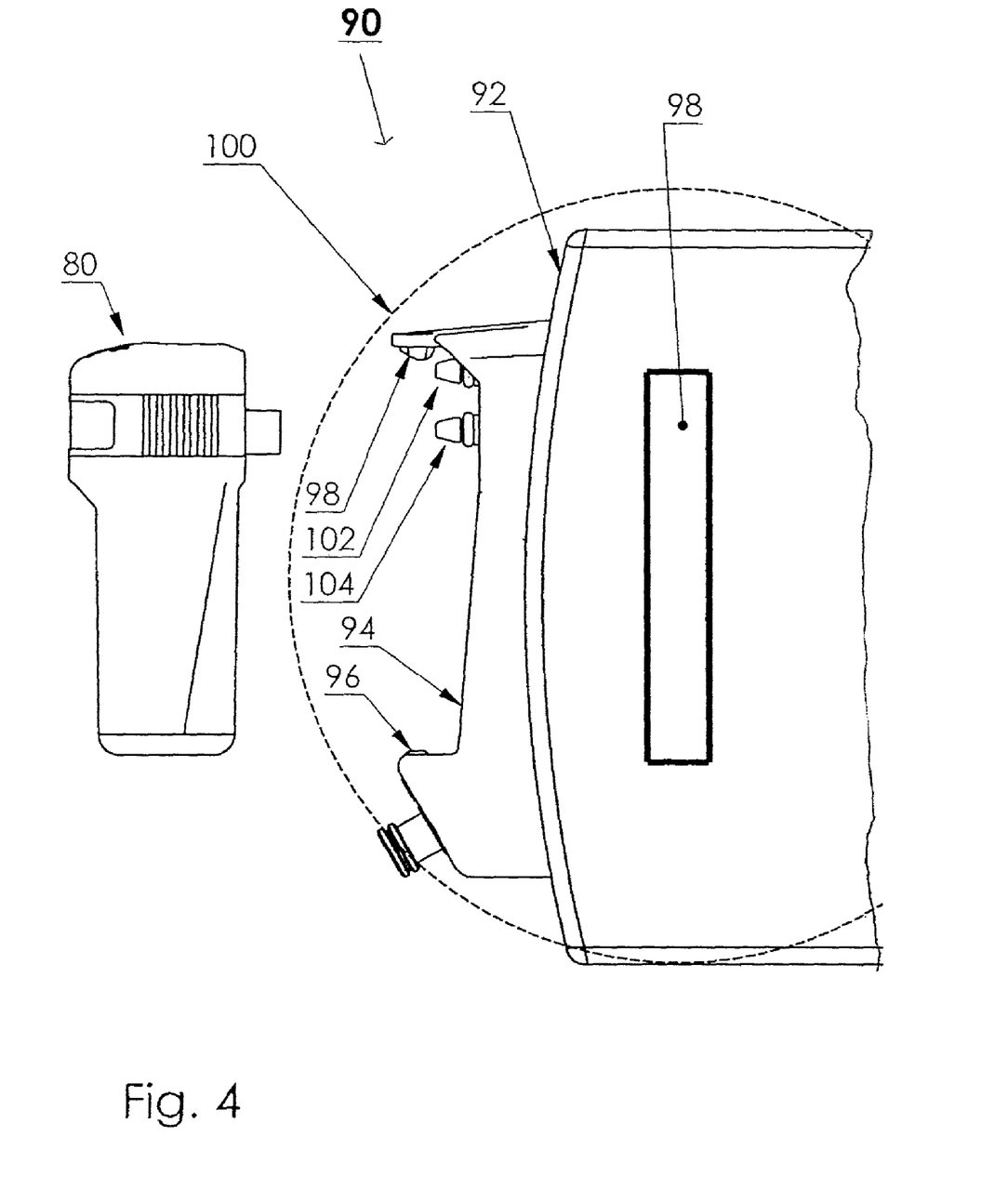
FIG. 4 is a schematic view showing an exemplary embodiment for a respiration means with a water trap shown in FIG. 3.

FIG. 4 schematically shows an embodiment of a respiration means 90 with a respiration device 92 and the water trap 80 shown in FIG. 3. The respiration device 92 has the radio frequency detection device 6 with a detection area 100 for the radio frequency marking 82, 84 or 86, which is designed to detect the radio frequency marking 82, 84 or 86 in the detection area 100 and to generate a marking signal, which represents a marking information of the radio frequency marking 82, 84 or 86. The respiration device 92 has a mount 94 for separable connection to the water trap 80. The mount has for this a cam 96 made integrally in one piece with a projection area, into which cam a correspondingly shaped area of a housing of the water trap 80 can be hung. The mount 94 also has a finger 98, which is made pivotable in one piece with the mount 94 and has a cam for meshing with a corresponding recess in the water trap 80 and is designed to mesh with the recess of the housing of the water trap 80 in a positive-locking manner after being pivoted into the recess of the housing and to secure same against separation. The finger may have a corresponding modulus of elasticity or a drag hinge for the pivoting. The respiration device 92 has a connection 102 for connection to a gas-carrying sample gas line and a connection 104 for connection to a gas-removing sample gas line.

While specific embodiments of the invention have been shown and described in detail to illustrate the application of the principles of the invention, it will be understood that the invention may be embodied otherwise without departing from such principles.

APPENDIX

List of Reference Numbers

1 Respiration device
2 Water trap
3 Gas sensor
4 Mount
5 Radio frequency marking
6 Radio frequency detection device
7 Detection area
9 Respirator
10 Central processor unit
12, 14 Memory
16, 18 Data set
20 Time counter
22 Timer
24 Sound generator
26 Signal light
28 Pump
30 Plug-type connection
32 Input unit
34 Touch-sensitive surface
36, 38 40, 42 Connection line
44, 46, 48, 50 Connection line
52 Connection line
54, 60, 62, 66 Sample gas line
56, 58 Respiration line
65 Filter membrane
68, 70 Opening
63 Cavity
64 Liquid
67 User's hand
70, 72, 74 Step
80 Water trap
82, 84, 86 Radio frequency marking
Liquid
90 Respiration means
92 Respiration device
94 Mount
96 Cam
98 Finger
100 Detection area
102, 104 Connection for a sample gas line

What is claimed is:

1. A device comprising:
a conduit carrying a sample gas flow;
a gas sensor;
a water trap mount;
a water trap detachably connected to said water trap mount, said water trap being connected to said conduit and to said gas sensor via said water trap mount, the sample gas flow being directed through said water trap to feed said sample gas flow to said gas sensor, said water trap being separably connected via said water trap mount for connection to and removal from the device;
a radio frequency marking associated with said water trap;
a data memory;
a radio frequency detection device with a detection area for detecting said radio frequency marking, wherein said radio frequency detection device detects said radio frequency marking in said detection area with said water trap connected to said water trap mount and said radio frequency detection device generates a marking signal with said water trap connected to said water trap mount in an initial connected state, said marking signal representing marking information and a connected state of said water trap mount and said water trap; and
a control unit controlling the device as a function of the marking signal, said control unit generating an initial time period corresponding to a duration of time during which said water trap is initially connected to the device as a function of detection of said marking signal, said control unit providing said initial time period as output to at least one of said radio frequency marking and said data memory, wherein said water trap is disconnected from said device in a disconnected state, said water trap being reconnected to said device in a reconnected state, said marking signal being generated via said radio frequency detection device with said water trap reconnected to said device in said reconnected state, said control unit comparing said initial time period in one of said data memory and said radio frequency marking with a predetermined run time period with said water trap and said device in said reconnected state, said control unit generating an additional time period corresponding to the duration of time during which said water trap is reconnected to the device as a function of detection of the marking signal, said additional time period comprising said initial time period, wherein said water trap does not operate with said additional time period being substantially equal to said predetermined time period.

2. A device in accordance with claim 1, further comprising a respiration device, said unit comprising:
a time counter operatively connected to said radio frequency detection device, said time counter generating said time period corresponding to the duration of time during which said water trap is connected to the device as a function of detection of the marking signal;
a comparison means for comparing said time period to said predetermined run time period and generating a comparison result; and
run signal means for generating, as a function of the comparison result, a run signal, said run signal representing a time course of the predetermined run time period, the respiration device being controlled as a function of the run signal.

3. A device in accordance with claim 1, wherein the control unit controlling the device includes blocking or releasing the device at least partially as a function of the marking signal.

4. A device in accordance with claim 2, wherein the run time period is represented by the marking information.

5. A device in accordance with claim 1, wherein the marking information of the radio frequency marking represents a code, which is assigned to said water trap.

6. A device in accordance with claim 1, wherein said water trap has a container for a liquid and said radio frequency marking is arranged within the container and can be subject to buoyancy in said liquid.

7. A device in accordance with claim 1, wherein said radio frequency marking receives marking information and stores the marking information in a readable form, said radio frequency detection device sending marking information to said radio frequency marking for storing marking information at the radio frequency marking.

8. A process for a device having a separably connected water trap, the process comprising the steps of:
providing a data memory;
detachably connecting the water trap to the device to define a connected state;
providing the water trap with a radio frequency marking;
detecting the radio frequency marking of the water trap and detecting marking information representing the radio frequency marking;
generating a marking signal representing the marking information and a connected state of said water trap with said device;
starting a time counter for incrementing a time value as a function of the marking signal with said device and said water trap in said connected state, wherein said time value corresponds to a time period of use of said water trap;
generating a run signal depending on whether a predetermined time value has been reached with said device and said water trap in said connected state;
controlling the device as a function of the run signal with said device and said water trap in said connected state;
stopping said time counter when said water trap is disconnected from said device or said time value is substantially equal to said predetermined time value; and
storing said time value with said marking information in at least one of said data memory and said radio frequency marking after said time counter is stopped.

9. A process in accordance with claim 8, wherein:
the device comprises a respiration device; and
said step of controlling includes at least partially blocking or releasing the respiration device as a function of the run signal.

10. A process in accordance with claim 8, wherein said step of controlling includes stopping or restarting of said time counter as a function of the marking signal.

11. A process in accordance with claim 10, further comprising:
sending the time value to the radio frequency marking; and
storing of the time value in the radio frequency marking after said time counter has been stopped.

12. A process in accordance with claim 9, further comprising:
providing the respiration device with a conduit carrying a sample gas flow, a gas sensor;
a water trap mount with the water trap connected to the respiration device via the water trap mount and with the water trap connected to the conduit and to the gas sensor;
directing the sample gas flow through the water trap to feed same to the gas sensor;
providing the respiration device with a radio frequency detection device with a detection area for detecting the radio frequency marking, wherein said step of detecting includes detecting the radio frequency marking in the detection area with the radio frequency detection device; and
generating a marking signal, which represents marking information.

13. A process in accordance with claim 9, further comprising:
disconnecting said water trap from said device to define a disconnected state;
reconnecting said water trap to said device to define a reconnected state;
detecting the radio frequency marking of the water trap and detecting marking information representing the radio frequency marking with said water trap and said device in said reconnected state;
comparing said time value with said predetermined time value;
incrementing said time counter from said time period with said water trap and said device in said reconnected state when said time value is less than said predetermined time value to define a continued time value;
stopping said time counter when said continued time value is substantially equal to said predetermined time value; and
disconnecting said water trap from said device when said continued time value is substantially equal to said predetermined time value.

14. A process in accordance with claim 13, wherein said marking signal is not generated when said water trap is disconnected from said device.

15. A device in accordance with claim 14, further comprising:
generating an alarm means when said continued time value is substantially equal to said predetermined time period.

16. A device in accordance with claim 2, wherein said run signal is not generated with said water trap disconnected from said device or with said time period being substantially equal to said predetermined time period.

17. A device in accordance with claim 2, further comprising an alarm means for generating an alarm when said sum of said additional time period and said time period is substantially equal to said predetermined time period.

18. A device in accordance with claim 17, wherein said water trap is connected to said water trap mount via a plug type connection.

19. A process in accordance with claim 13, wherein said water trap is connected to said device via a plug type connection.

* * * * *